United States Patent
Yamaguchi et al.

(10) Patent No.: US 11,453,633 B2
(45) Date of Patent: Sep. 27, 2022

(54) PRODUCTION METHOD FOR CRYSTAL OF REDUCED COENZYME Q10 HAVING EXCELLENT STABILITY

(71) Applicant: KANEKA CORPORATION, Osaka (JP)

(72) Inventors: Takao Yamaguchi, Takasago (JP); Koichi Kinoshita, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 17/271,735

(22) PCT Filed: Aug. 29, 2019

(86) PCT No.: PCT/JP2019/033923
§ 371 (c)(1),
(2) Date: Feb. 26, 2021

(87) PCT Pub. No.: WO2020/045571
PCT Pub. Date: Mar. 5, 2020

(65) Prior Publication Data
US 2021/0317057 A1    Oct. 14, 2021

(30) Foreign Application Priority Data
Aug. 30, 2018    (JP) .............................. JP2018-161790

(51) Int. Cl.
*C07C 41/40*    (2006.01)
(52) U.S. Cl.
CPC .......... *C07C 41/40* (2013.01); *C07B 2200/13* (2013.01)

(58) Field of Classification Search
CPC ...... C07C 41/40; C07C 46/10; C07B 2200/13
See application file for complete search history.

(56) References Cited

U.S. PATENT DOCUMENTS

| 6,184,255 | B1 | 2/2001 | Mae et al. |
| 2004/0214301 | A1 | 10/2004 | Ueda et al. |
| 2014/0120073 | A1 | 5/2014 | Kawachi et al. |
| 2015/0284311 | A1* | 10/2015 | Kawachi ................. C07C 46/10 552/307 |

FOREIGN PATENT DOCUMENTS

| JP | 10-109933 A | 4/1998 |
| JP | 2003-89669 A | 3/2003 |
| WO | WO 03/006409 A1 | 1/2003 |
| WO | WO 2012/176842 A1 | 12/2012 |

* cited by examiner

*Primary Examiner* — Rosalynd A Keys
(74) *Attorney, Agent, or Firm* — Birch, Stewart, Kolasch & Birch, LLP

(57) ABSTRACT

Provided is a production method capable of efficiently producing a reduced coenzyme Q10 Form II crystal. The method for producing a reduced coenzyme Q10 Form II crystal includes: adding a reduced coenzyme Q10 Form II crystal as a seed crystal to a solution with a temperature of 32° C. to 43° C., the solution containing fa) at least one organic solvent selected from the group consisting of an alcohol, a hydrocarbon, an aliphatic acid ester and a nitrogen compound, and (b) reduced coenzyme Q10, to prepare a mixture, and precipitating the reduced coenzyme Q10 from the mixture, in the form of the reduced coenzyme Q10 Form II crystal.

15 Claims, No Drawings

PRODUCTION METHOD FOR CRYSTAL OF REDUCED COENZYME Q10 HAVING EXCELLENT STABILITY

TECHNICAL FIELD

The present invention relates to a reduced coenzyme Q10 crystal excellent in stability and a method for producing reduced coenzyme Q10 containing large quantities of the aforementioned crystals.

BACKGROUND ART

Coenzyme Q is an essential component widely distributed in living organisms from bacteria to mammals, and is known as a member of mitochondrial electron transfer system in cells in the living organisms. Coenzyme Q engages in electron transfer in the electron transfer system by the repetition of oxidation and reduction in mitochondria. Further, reduced coenzyme Q is known to have antioxidant activity. The major component in humans is coenzyme Q10 which is one having 10 repeating structures in the side chain of coenzyme Q, and usually, about 40% to 90% thereof is present in the living body as the reduced form. The physiological activity of coenzyme Q includes activation of energy production by mitochondrial activation, activation of cardiac function, an effect of stabilizing cell membranes, and an effect of protecting cells by antioxidant activity.

While coenzyme Q10 currently produced and sold is, in large part, oxidized coenzyme Q10, reduced coenzyme Q10 which exhibits higher oral absorbability than that of oxidized coenzyme Q10 has also been commercially available and has come to be used in recent years.

A common method for obtaining reduced coenzyme Q10 has already been disclosed (Patent Literature 1). Furthermore, several methods for obtaining reduced coenzyme Q10 as a crystal have also been known. For example, a method of crystallizing reduced coenzyme Q10 in an alcohol solution and/or a ketone solution to produce a crystal (Patent Literature 2), a method of adding a high concentration liquid phase of reduced coenzyme Q10 into a poor solvent for crystallization (Patent Literature 3), and the like have been reported.

On the other hand, Patent Literature 4 reports that crystal polymorphism is found in reduced coenzyme Q10. It reports that a newly found crystal form (this crystal is hereinafter referred to as a "reduced coenzyme Q10 Form II crystal") is much more stable and more excellent in other physical properties than the conventional reduced coenzyme Q10 (this crystal is hereinafter referred to as a "reduced coenzyme Q10 Form I crystal").

CITATION LIST

Patent Literature

Patent Literature 1: JP Patent Publication No. 10-109933 A (1998)
Patent Literature 2: WO2003-006409
Patent Literature 3: JP Patent Publication No. 2003-089669 A (2003)
Patent Literature 4: WO2012-176842

SUMMARY OF INVENTION

Technical Problem

Patent Literature 4 discloses a method for obtaining a reduced coenzyme Q10 Form II crystal, in which crystallization is carried out under specific conditions. However, there is a case where it takes a long period of time and further, the recovered amount is small. Thus, the method is not necessarily industrially optimal. Moreover, Patent Literature 4 also discloses a method of using a reduced coenzyme Q10 Form II crystal as a seed crystal upon crystallization. The present inventors have examined this method. As a result, it has been found that there is a case where the yield of the reduced coenzyme Q10 Form II crystal is low or such a reduced coenzyme Q10 Form II crystal cannot be obtained depending on crystallization conditions. Hence, the present inventors have found that conducting further studies, for example, regarding reproducibility is necessary in order to efficiently produce a reduced coenzyme Q10 Form II crystal.

Accordingly, it is an object of the present invention to provide an efficient method for producing a reduced coenzyme Q10 Form II crystal, which is a stable crystal form, the method being suitable for industrial scale production.

Solution to Problem

As a result of intensive studies directed towards achieving the aforementioned object, the present inventors have found that a reduced coenzyme Q10 Form II crystal can be produced with good reproducibility and high efficiency by a crystal precipitation method in which a reduced coenzyme Q10 Form II crystal is used as a seed crystal, a specific solvent is used and the seed crystal is added to the specific solvent in a specific temperature range. Based on this finding, the present inventors have completed the present invention.

Specifically, the method for producing a reduced coenzyme Q10 Form II crystal of the present invention is characterized in that it comprises:

adding a reduced coenzyme Q10 Form II crystal as a seed crystal to a solution with a temperature of 32° C. to 43° C., containing at least one organic solvent selected from the group consisting of an alcohol, a hydrocarbon, an aliphatic acid ester and a nitrogen compound, and reduced coenzyme Q10, to prepare a mixture, and precipitating a reduced coenzyme Q10 Form II crystal in the mixture.

In one or more preferred aspects of the present invention, the amount of the seed crystal added is 0.5% to 20% by weight, based on the weight of the reduced coenzyme Q10 in the solution before the addition of the seed crystal.

In one or more other preferred aspects of the present invention, the organic solvent comprises 0.5% to 34% by weight of water.

In one or more other preferred aspects of the present invention, the organic solvent is a monohydric alcohol having 1 to 5 carbon atoms. Further, the above-described alcohol is preferably ethanol. Further, the ethanol preferably comprises 8% by weight or less of water or does not comprise water.

One or more other preferred aspects of the present invention further comprise, before the preparation of the mixture, heating a raw material mixture containing the organic solvent and the reduced coenzyme Q10 to 42° C. or higher, so that the reduced coenzyme Q10 is dissolved therein, and cooling the solution after the heating to a temperature that is lower than the heating temperature and in the range of 32° C. to 43° C., to prepare a supersaturated solution of the reduced coenzyme Q10.

In one or more other preferred aspects of the present invention, the precipitating the crystal comprises maintaining the temperature of the mixture at 32° C. or higher for 1 hour or more after the adding the seed crystal.

In one or more other preferred aspects of the present invention, the precipitating the crystal comprises decreasing over time the temperature of the mixture.

In one or more other preferred aspects of the present invention, the precipitating the crystal comprises:

maintaining the temperature of the mixture at 32° C. or higher for 1 hour or more after the adding the seed crystal, and then, decreasing the temperature of the mixture to a temperature of 25° C. or lower at a rate in which a temperature decrease amount per hour is 15° C. or lower.

In one or more other preferred aspects of the present invention, the precipitating the crystal is carried out, while forced-flowing the mixture with a power required for stirring of 0.03 kw/m³ or more per unit volume.

In one or more other preferred aspects of the present invention, the solution contains 1% by weight or more and 70% by weight or less of reduced coenzyme Q10.

One or more other preferred aspects of the present invention further comprise solid-liquid separating the precipitated crystal and then drying the precipitated crystal at a temperature of 46° C. or higher.

In one or more other preferred aspects of the present invention, each step is carried out under a deoxygenated atmosphere.

The present description encompasses the specification and/or drawings in JP Patent Application No. 2018-161790 which serves as the basis of the priority of the present application.

Advantageous Effects of Invention

According to the production method of the present invention, a reduced coenzyme Q10 Form II crystal that is more stable than the conventional reduced coenzyme Q10 crystal can be produced by an efficient and industrially suitable method.

DESCRIPTION OF EMBODIMENTS

Hereinafter, the present invention will be described in detail. The "reduced coenzyme Q10" herein may partially include oxidized coenzyme Q10, if it includes reduced coenzyme Q10 as a main component. The "main component" herein means that it is included in a proportion of, for example, 50% by weight or more, usually 60% by weight or more, preferably 70% by weight or more, more preferably 80% by weight or more, further preferably 90% by weight or more, particularly preferably 95% by weight or more, and further particularly preferably 98% by weight or more. Herein, the above-described percentage is the percentage of the reduced coenzyme Q10 to the total weight of coenzyme Q10

Besides, as mentioned above, the reduced coenzyme Q10 includes two types of crystal polymorphisms, namely, the conventionally known Form I and a recently newly found Form II. Specifically, the crystal form of reduced coenzyme Q10 having a melting point around 48° C. and showing characteristic peaks at diffraction angles (2θ±0.2°) of 3.1°, 18.7°, 19.0°, 20.2° and 23.0° in powder X-ray (Cu-Kα) diffraction is Form I, whereas the crystal form of reduced coenzyme Q10 having a melting point around 52° C. and showing characteristic peaks at diffraction angles (2θ±0.2°) of 11.5°, 18.2°, 19.3°, 22.3°, 23.0° and 33.3° in powder X-ray (Cu-Kα) diffraction is Form II. In the present description, the crystal of reduced coenzyme Q10 that satisfies at least one of the following conditions is referred to as a "reduced coenzyme Q10 Form II crystal": when the temperature is increased at a rate of 5° C./min by differential scanning calorimetry (DSC), the reduced coenzyme Q10 crystal has an endothermic peak at 54±2° C.; when the same measurement is carried out at a temperature rising rate of 1° C./min, the reduced coenzyme Q10 crystal has an endothermic peak at 52±2° C.; and in powder X-ray (Cu-Kα) diffraction, the reduced coenzyme Q10 crystal shows characteristic peaks at diffraction angles (2θ±0.2°) of 11.5°, 18.2°, 19.3°, 22.3°, 23.0° and 33.3°. Of course, the reduced coenzyme Q10 crystal may satisfy all of said three conditions.

Moreover, the term "crystalline solid" is used in the present description to mean a solid containing therein a portion having a crystal structure and an amorphous portion having no crystal structure.

The method for producing a reduced coenzyme Q10 Form II crystal of the present invention is characterized in that it comprises:

adding a reduced coenzyme Q10 Form II crystal as a seed crystal to a solution with a temperature of 32° C. to 43° C., containing at least one organic solvent selected from the group consisting of an alcohol, a hydrocarbon, an aliphatic acid ester and a nitrogen compound, and reduced coenzyme Q10, to prepare a mixture, and precipitating a reduced coenzyme Q10 Form II crystal in the mixture.

The solution containing an organic solvent and reduced coenzyme Q10, which is used in the present invention, is not particularly limited, as long as it contains reduced coenzyme Q10. Thus, the solution may be either in a homogeneous solution state in which the reduced coenzyme Q10 is dissolved in the organic solvent used, or in a slurry state in which a part of the reduced coenzyme Q10 is not dissolved and remains as is. The solution is preferably in a homogeneous solution state.

Besides, the reduced coenzyme Q10 used for preparing the above-described reduced coenzyme Q10-containing solution may be either a crystalline or amorphous state, and the crystal polymorphism thereof is not limited. Accordingly, the conventionally known reduced coenzyme Q10 Form I can also be used. In addition, since the purity of the reduced coenzyme Q10 can be increased in precipitation of a crystal, reduced coenzyme Q10 having impurities, or unpurified or roughly purified reduced coenzyme Q10 may also be used. Furthermore, an extract of the reduced coenzyme Q10 obtained by a conventionally known method, or a reaction solution containing reduced coenzyme Q10 obtained from oxidized coenzyme Q10 by a known reduction method may also be used as the reduced coenzyme Q10-containing solution, directly, or after purification and/or solvent substitution, as necessary.

In the present invention, as an organic solvent used in the reduced coenzyme Q10-containing solution, at least one organic solvent selected from the group consisting of an alcohol, a hydrocarbon, an aliphatic acid ester and a nitrogen compound needs to be used.

The alcohol used in the present invention may be cyclic or acyclic, or may be saturated or unsaturated, and is not particularly limited, but in general, a saturated alcohol is preferably used. For example, a monohydric alcohol having 1 to 20 carbon atoms, 1 to 12 carbon atoms, preferably 1 to 6, more preferably 1 to 5 carbon atoms, further preferably 1 to 4 carbon atoms, still further preferably 1 to 3 carbon atoms, and particularly preferably 2 or 3 carbon atoms, or a dihydric alcohol having 2 to 5 carbon atoms is preferable, or a trihydric alcohol having 3 carbon atoms is preferable. Among the above-described alcohols, a monohydric alcohol having 1 to 5 carbon atoms is highly miscible with water, and thus, the monohydric alcohol having 1 to 5 carbon atoms is preferably used in the form of a mixed solvent with water.

Examples of the monohydric alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, and 4-methylcyclohexanol.

Preferred examples of the monohydric alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, and cyclohexanol; and more preferred examples thereof include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, and neopentyl alcohol. The monohydric alcohol is further preferably methanol, ethanol, 1-propanol, 2-propanol, 1-butanol, 2-butanol, isobutyl alcohol, 2-methyl-1-butanol, or isopentyl alcohol; is particularly preferably methanol, ethanol, 1-propanol, or 2-propanol; is further particularly preferably ethanol, 1-propanol, or 2-propanol; and is most preferably ethanol.

Examples of the dihydric alcohol include 1,2-ethanediol, 1,2-propanediol, 1,3-propanediol, 1,2-butanediol, 1,3-butanediol, 1,4-butanediol, 2,3-butanediol, and 1,5-pentanediol. The dihydric alcohol is preferably 1,2-ethanediol, 1,2-propanediol, or 1,3-propanediol; and is most preferably 1,2-ethanediol.

As a trihydric alcohol, glycerin or the like can be preferably used.

Examples of the hydrocarbons include, but are not particularly limited to, aliphatic hydrocarbon, aromatic hydrocarbon, and halogenated hydrocarbon.

The aliphatic hydrocarbon to be used may be cyclic or acyclic, or may be saturated or unsaturated, and is not particularly limited, but is usually one having 3 to 20 carbon atoms, preferably one having 5 to 12 carbon atoms. Specific examples thereof include propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane and dodecane. The aliphatic hydrocarbon is preferably pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, and p-menthane. More preferred examples thereof include pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, and ethylcyclohexane. The aliphatic hydrocarbon is further preferably pentane, hexane, cyclohexane, methylcyclohexane or the like, is particularly preferably heptane, hexane or methylcyclohexane, and is most preferably heptane or hexane.

The aromatic hydrocarbon to be used is not particularly limited, but is usually one having 6 to 20 carbon atoms, preferably one having 6 to 12 carbon atoms, and more preferably one having 7 to 10 carbon atoms. Specific examples thereof include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene and styrene.

The halogenated hydrocarbon to be used may be cyclic or acyclic, or may be saturated or unsaturated, and is not particularly limited, but is preferably acyclic one. More preferred halogenated hydrocarbon is chlorinated hydrocarbon or fluorinated hydrocarbon, and further preferred halogenated hydrocarbon is chlorinated hydrocarbon.

In addition, the halogenated hydrocarbon to be used is one having 1 to 6 carbon atoms, preferably one having 1 to 4 carbon atoms, more preferably one having 1 or 2 carbon atoms. Specific examples thereof include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene and 1,1,1,2-tetrafluoroethane.

Examples of the aliphatic acid esters include, but are not particularly limited to, propionic acid ester, acetic acid ester, and formic acid ester. Preferred is acetic acid ester or formic acid ester, and more preferred is acetic acid ester.

Examples of an ester group include, but are not particularly limited to, an alkyl ester having 1 to 8 carbon atoms and an aralkyl ester having 1 to 8 carbon atoms. The ester group is preferably an alkyl ester having 1 to 6 carbon atoms and is more preferably an alkyl ester having 1 to 4 carbon atoms.

Examples of the propionic acid ester include methyl propionate, ethyl propionate, butyl propionate, and isopentyl propionate.

Examples of the acetic acid ester include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Preferred examples thereof include methyl acetate, ethyl acetate, propyl acetate, isopropyl acetate, butyl acetate, and isobutyl acetate. Most preferred is ethyl acetate.

Examples of the formic acid ester include methyl formate, ethyl formate, propyl formate, isopropyl formate, butyl formate, isobutyl formate, sec-butyl formate, and pentyl formate.

As a nitrogen compound, for example, nitrile can be used. The nitrile may be cyclic or acyclic, or may be saturated or unsaturated, and is not particularly limited, but a saturated nitrile is preferably used. In general, a nitrile having 2 to 20 carbon atoms, preferably 2 to 12 carbon atoms, and more preferably 2 to 8 carbon atoms is used. Specific examples of the nitriles include acetonitrile, propionitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, and tolylcyclohexanecarbonitrile. Preferred examples thereof include acetonitrile, propionitrile, succinonitrile, butyronitrile, isobutyronitrile, valeronitrile, methyl cyanoacetate, ethyl cyanoacetate, benzonitrile, tolunitrile, and chloropropionitrile; more preferred examples thereof include acetonitrile, propionitrile, butyronitrile, and isobutyronitrile; and the nitrile is most preferably acetonitrile.

Examples of the nitrogen compounds other than the above-described nitriles include nitromethane, triethylamine, pyridine, formamide, N-methylformamide, N,N-dimethylformamide, N,N-dimethylacetamide, and N-methylpyrrolidone.

Among the above-described organic solvents, alcohol or hydrocarbon is preferable, and alcohol is particularly preferable.

In the present invention, as an organic solvent used for preparing the reduced coenzyme Q10-containing solution, the above-exemplified organic solvents may be used alone, or in order to improve the conditions which affect crystal precipitation conditions, such as the solubility, crystal precipitation concentration, yield, slurry properties and/or crystalline properties of reduced coenzyme Q10, two or more types of the solvents may be used with being mixed in a preferable proportion, according to the properties of each solvent.

Moreover, as long as the above-described at least one organic solvent selected from the group consisting of an alcohol, a hydrocarbon, an aliphatic acid ester and a nitrogen compound is used, other organic solvents may also be used in combination. Furthermore, the "organic solvent" used in the present invention includes organic solvents containing water. In order to improve conditions such as the yield, slurry properties and crystalline properties of the obtained reduced coenzyme Q10, and the content of a QH Form II crystal, the above-described organic solvent containing water can be used. In such a case, the water amount in the organic solvent is preferably 0.01% to 50% by weight, more preferably 0.1% to 40% by weight, further preferably 0.5% to 34% by weight, and particularly preferably 0.5% to 15% by weight, based on the total amount of the organic solvent containing water. If the water amount in the organic solvent is 50% by weight or more, there is a case where separation between the organic solvent and the water may occur, or the solubility of the reduced coenzyme Q10 in the organic solvent may be significantly reduced, so that crystallization of the reduced coenzyme Q10 containing a large amount of desired QH Form II may become difficult. In the case of using such an organic solvent containing water, the water and the organic solvent are preferably in a homogeneous phase. Even from this viewpoint, as an organic solvent, alcohol such as ethanol, or aliphatic acid ester such as ethyl acetate is preferably selected.

In more preferred one or more embodiments of the present invention, the organic solvent is a monohydric alcohol having 1 to 5 carbon atoms that contains 15% by weight or less of water or does not contain water, is more preferably a monohydric alcohol having 1 to 5 carbon atoms that contains 8% by weight or less of water or does not contain water, is particularly preferably ethanol containing 8% by weight or less of water or does not contain water, and is further particularly preferably ethanol containing 0.1% by weight or more and 8% by weight or less of water.

The concentration of the reduced coenzyme Q10 in the above-described solution comprising the organic solvent and the reduced coenzyme Q10 is not particularly limited, and can be appropriately adjusted depending on the organic solvent used. For example, the concentration of the reduced coenzyme Q10 is 80% by weight or less, preferably 70% by weight or less, more preferably 60% by weight or less, further preferably 50% by weight or less, and particularly preferably 40% by weight or less. Further, in terms of production efficiency, the concentration of the reduced coenzyme Q10 in the above-described solution is preferably adjusted to somewhat a high concentration, and for example, it is preferably 1% by weight or more, more preferably 5% by weight or more, and particularly preferably 10% by weight or more.

The above-described solution containing the organic solvent and the reduced coenzyme Q10, which is used to prepare the mixture to be subjected to a crystal precipitation step after the addition of a seed crystal thereto is more preferably a supersaturated solution comprising reduced coenzyme Q10 that is dissolved therein at the saturated concentration of the reduced coenzyme Q10 or higher in the temperature for preparation of the mixture between 32° C. and 43° C. Such a supersaturated solution is obtained by heating a raw material mixture containing the above-described organic solvent and reduced coenzyme Q10 to a temperature of 42° C. or higher, 45° C. or higher, more preferably 49° C. or higher, further preferably 70° C. or lower, particularly preferably 55° C. or lower, so that the reduced coenzyme Q10 is dissolved, and then cooling the heated solution down to a temperature that is lower than the above-described heating temperature and in the temperature range of 32° C. to 43° C. to prepare a supersaturated solution of the reduced coenzyme Q10.

In particular, in an embodiment in which the above-described organic solvent is a monohydric alcohol having 1 to 5 carbon atoms (preferably, ethanol) that contains 8% by weight or less of water or does not contain water, the concentration of the reduced coenzyme Q10 in the above-described solution comprising the organic solvent and the reduced coenzyme Q10 is preferably 5% by weight or more, and more preferably 10% by weight or more; on the other hand, it is preferably 50% by weight or less, more preferably 40% by weight or less, further preferably 25% by weight or less, and particularly preferably 20% by weight or less. When the reduced coenzyme Q10 comprised in the above-described solution is in this concentration range, a supersaturated solution of the reduced coenzyme Q10 is easily prepared according to the aforementioned procedures, and the Form II crystal is easily precipitated by addition of the seed crystal.

In the present invention, reduced coenzyme Q10 Form II crystals are added as seed crystals to the above-described solution comprising the organic solvent and the reduced coenzyme Q10, so as to prepare a mixture to be subjected to a crystal precipitation step. The added amount of the reduced coenzyme Q10 Form II crystals used as seed crystals (the added amount of seed crystals) is not particularly limited. The added amount of the reduced coenzyme Q10 Form II crystals used as seed crystals is preferably 0.1% to 30% by weight, more preferably 0.5% to 20% by weight, and particularly preferably 0.8% to 5% by weight, based on the amount of the reduced coenzyme Q10 in the reduced coenzyme Q10-containing solution before the addition of the seed crystals. Besides, the reduced coenzyme Q10 crystals used as seed crystals may also comprise reduced coenzyme Q10 Form I crystals or amorphous solids, as long as the reduced coenzyme Q10 crystals comprise reduced coenzyme Q10 Form II crystals. However, the reduced coenzyme Q10 crystals comprising reduced coenzyme Q10 Form II crystals having a high purity are preferable. Thus, it may be preferable to use the reduced coenzyme Q10 crystals comprising, for example, 50% by weight or more of, preferably 75% by weight or more of, more preferably 80% by weight or more of, and further preferably 90% by weight or more of reduced coenzyme Q10 Form II crystals.

Further, the present invention is characterized in that the temperature of the reduced coenzyme Q10-containing solution is in the range of 32° C. to 43° C., when the seed crystals are added thereto. The temperature of the reduced coenzyme Q10-containing solution upon addition of the seed crystals is preferably 35° C. or higher, and more preferably 38° C. or higher. The upper limit of the temperature is preferably 41° C. or lower. When the temperature of the reduced coenzyme Q10-containing solution upon addition of the seed crystals exceeds 43° C., the added seed crystals may be dissolved and crystals may not be precipitated in some cases. On the other hand, when the seed crystals are added to the reduced coenzyme Q10-containing solution at a temperature of lower than 32° C., the percentage of the Form II crystals in the precipitated reduced coenzyme Q10 may become low or the Form II crystals may not be precipitated in some cases.

Subsequently, one or more preferred embodiments of a crystal precipitation step of precipitating reduced coenzyme Q10 Form II crystals in the above-described mixture will be described. As long as the temperature of the reduced coenzyme Q10-containing solution upon addition of the seed crystals is within the above-described range, the temperature applied in the crystal precipitation step after the addition of the seed crystals is not particularly limited. Preferably, the temperature of the mixture is maintained preferably at 32° C. or higher, more preferably in the range of 32° C. to 43° C., for 1 hour or more after the addition of the seed crystals. The above-described temperature range is more preferably selected from the same range as the preferred range of the temperature of the solution upon addition of the seed crystals. The period of time, in which the mixture is maintained in the above-described temperature range, is not particularly limited, but it is preferably 1 hour or more, more preferably 2 hours or more, further preferably 4 hours or more, and particularly preferably 10 hours or more. The upper limit of the period of time, in which the mixture is maintained in the above-described temperature range, is not particularly limited, but sufficient effects are obtained by maintaining the mixture in the above-described temperature range for approximately 24 hours. In this case, the mixture may be maintained at a constant temperature, for example, at a temperature in the range of 32° C. to 43° C., or after the addition of seed crystals, the mixture may be gradually cooled, for example, in cooling crystallization, and the temperature may then reach 32° C. Otherwise, a temperature from 32° C. to 43° C. may be maintained through a crystal precipitation step, or a temperature from 32° C. to 43° C. may be maintained, for example for 1 hour or more, and thereafter, the mixture may be cooled.

The end-point temperature of the crystal precipitation step is not particularly limited. From the viewpoint of an increase in the recovery amount, the crystal precipitation step is carried out preferably at 40° C. or lower, more preferably at 35° C. or lower, and particularly preferably at 30° C. or lower. The lower limit is the solidification temperature of the mixture, and is preferably 0° C. or higher, more preferably 10° C. or higher.

In the crystal precipitation step, the formation of supersaturation is preferably regulated by controlling the amount of crystals precipitated per unit time. The preferred amount of crystals precipitated per unit time is, for example, the rate of precipitating approximately 50% or lower of the total amount of crystals precipitated per hour (i.e., at maximum, 50% amount/hour), and is preferably the rate of precipitating approximately 25% or lower of the total amount of crystals precipitated per hour (i.e., at maximum, 25% amount/hour)

In one or more preferred embodiments, the above-described crystal precipitation step comprises a step of decreasing over time the temperature of the mixture, namely, a step of cooling crystallization. In the cooling crystallization, crystallization is promoted by cooling the mixture to decrease the solubility of the reduced coenzyme Q10 in the liquid phase of the mixture. The step of cooling the mixture is preferably carried out immediately after the above-described step of maintaining the mixture at a temperature of 32° C. or higher for a certain period of time to precipitate crystals that can be precipitated at this temperature. The above-described "decreasing over time the temperature of the mixture" includes continuously decreasing the temperature of the mixture as time passes, decreasing stepwise the temperature of the mixture, and a combination thereof. In the case of decreasing the temperature of the mixture over time, the cooling rate is not particularly limited. For example, it is a cooling rate, in which the temperature decrease amount per hour is 30° C. or lower, preferably 20° C. or lower, more preferably 15° C. or lower, even more preferably 10° C. or lower, and further preferably 5° C. or lower, and also, it is preferably 1° C. or higher, and more preferably 2° C. or higher. When the temperature of the mixture is decreased over time, the cooling rate may be either constant or varied. In particular, according to an embodiment in which the above-described cooling rate continuously or stepwise increases, namely, the temperature decrease amount per hour increases, as the temperature of the mixture decreases, the reduced coenzyme Q10 whose amount remaining in the liquid phase decreases as the temperature of the mixture decreases can be efficiently crystallized. For example, until the temperature of the mixture reaches 25° C., the mixture can be cooled at a rate in which the temperature decrease amount per hour is preferably 5° C. or lower, and more preferably 3° C. or lower. Then, at the stage in which the mixture is further cooled to lower than 25° C., the mixture can be cooled at a rate in which the temperature decrease amount per hour is preferably 6° C. or higher, and more preferably 8° C. or higher. In one or more embodiments of the present invention, the end-point temperature that is reached by decreasing the temperature of the mixture over time is preferably 25° C. or lower, more preferably 20° C. or lower, even more preferably 10° C. or lower, further preferably 7° C. or lower, and still further preferably 5° C. or lower. The lower limit of the above-described end-point temperature is the solidification temperature of the system of the mixture, and is preferably 0° C. or higher, and more preferably 3° C. or higher.

Precipitation of crystals is preferably carried out, while forced-flowing the mixture after the addition of the seed crystals. In order to suppress the formation of supersaturation and smoothly conduct nucleation and/or crystal growth, or from the viewpoint of the achievement of high quality, flowing may be given to the mixture at a power required for stirring per unit volume of generally approximately 0.01 kW/m$^3$ or more, preferably 0.03 kW/m$^3$ or more, more preferably 0.1 kW/m$^3$ or more, and further preferably 0.3 kW/m$^3$ or more. The forced-flowing is generally given by the rotation of a stirring blade. However, if the above-described flowing is obtained, the use of the stirring blade is not always necessary, and for example, a method involving circulation of the mixture may be utilized.

In the production method of the present invention, the preferred crystal precipitation method is not particularly limited. In addition to the above-described cooling crystallization, poor solvent crystallization, concentration crystallization, etc. can be utilized. Among others, cooling crystallization or a method involving a combination of cooling crystallization with another crystallization method is preferable. The poor solvent crystallization is a method of crystallizing the reduced coenzyme Q10 by mixing a poor solvent into the above-described mixture to decrease solubility. Herein, the poor solvent means a solvent in which the reduced coenzyme Q10 is hardly or completely not dissolvable. The poor solvent and the organic solvent used for the reduced coenzyme Q10-containing solution are preferably mutually dissolved in each other.

As such a method of mixing the mixture with the poor solvent, the poor solvent may be added into the solution, or the solution may be added into the poor solvent. In addition to the above-described poor solvent crystallization, another crystallization method combined with cooling crystallization is, for example, concentration crystallization in which crystals are precipitated by concentrating the solution.

The reduced coenzyme Q10 Form II crystal or crystalline solid obtained by the above method is recovered through a step of solid-liquid separation and drying by a conventionally known method described in, for example, Patent Literature 2 or 3. For example, pressure filtration or centrifugal filtration can be used for solid-liquid separation. In addition, the crystal or crystalline solid after drying can also be recovered by pulverization or classification (sieving), if necessary.

In the present invention, as one of more preferred aspects, after completion of the aforementioned solid-liquid separation, the reduced coenzyme Q10 Form II crystal or the crystalline solid is dried with warming, so that the content of the reduced coenzyme Q10 Form II crystal can be improved. For this purpose, the drying temperature is preferably 46° C. or higher, more preferably 47° C. or higher, and further preferably 49° C. or higher. The upper limit of the drying temperature is generally 52° C. or lower, and preferably 51° C. or lower. When the drying temperature is lower than 46° C., which may be sufficient for progressing the drying, the content of the reduced coenzyme Q10 Form II crystal is hardly improved. On the other hand, when the drying temperature exceeds 52° C., there may be a case where the reduced coenzyme Q10 crystal is melted during the drying. In addition, the warming time in the case of performing drying under the aforementioned conditions is not particularly limited, but it is preferably 4 hours or more, more preferably 10 hours or more, and further preferably 20 hours or more.

Besides, when the desired content of the reduced coenzyme Q10 Form II crystal has already been achieved in the crystal precipitation step, the aforementioned drying conditions shall not apply, and the drying may be carried out at a temperature of, for example, 25° C. or higher, preferably 30° C. or higher, and more preferably 35° C. or higher.

Besides, individual steps in the method of the present invention, specifically, the above-described mixture forming step, crystal precipitation step, recovery step such as solid-liquid separation or drying, and other treatment steps are preferably performed under a deoxygenated atmosphere. The deoxygenated atmosphere can be achieved by the replacement of the atmosphere with an inert gas, reduction of the pressure, boiling, or a combination thereof. The replacement of the atmosphere with an inert gas, namely, an inert gas atmosphere is preferably used. Examples of the inert gas include nitrogen gas, helium gas, argon gas, hydrogen gas, and carbon dioxide, and preferred is nitrogen gas.

Whether or not the reduced coenzyme Q10 Form II crystal is contained in the obtained reduced coenzyme Q10 crystal or crystalline solid, and the content thereof can be determined by measuring with, for example, a differential scanning calorimeter (DSC).

As mentioned above, when the reduced coenzyme Q10 Form II crystal is measured with DSC at a temperature rising rate of 1° C./min, it exhibits an endothermic peak around 52±2° C. On the other hand, the reduced coenzyme Q10 Form I crystal exhibits an endothermic peak around 48±1° C. under the same conditions as those described above. Even in a state in which the reduced coenzyme Q10 Form II crystal is mixed with the conventional reduced coenzyme Q10 Form I crystal or a crystalline solid thereof, the presence or absence of the reduced coenzyme Q10 Form II crystal or the content thereof can be determined based on the presence or absence of the above-described peak around 52±2° C., the height of the endothermic peak, or the ratio of the endothermic energy amount. According to the method of the present invention, a reduced coenzyme Q10 Form II crystal or a crystalline solid having a high purity can be efficiently obtained.

EXAMPLES

Hereinafter, the present invention will be more specifically described with reference to Examples. However, the technical scope of the present invention is not intended to be limited to these Examples. It is to be noted that the measurement conditions of DSC in Examples and Comparative Examples are as follows.

(DSC Measurement Conditions)
Apparatus: DSC 6220, manufactured by SII Nano Technology Inc.
Sample container: Aluminum pan & cover (SSC000C008)
Rate of temperature rise: 1° C./min
Amount of sample: 5±2 mg From the height (Difference Y) of the endothermic peak of a reduced coenzyme Q10 Form I crystal obtained by DSC analysis (hereinafter referred to as "Difference I-Y") and the height (Difference Y) of the endothermic peak of a reduced coenzyme Q10 Form II crystal obtained by DSC analysis (hereinafter referred to as "Difference II-Y"), the percentage of the reduced coenzyme Q10 Form II crystal (Form II rate) was calculated as follows.

$$\text{Form } II \text{ rate } (\%) = \frac{(\text{Difference } II - Y)}{(\text{Difference } I - Y) + (\text{Difference } II - Y)} \times 100 \quad \text{[Formula 1]}$$

Example 1

The inside of a 500 mL separable flask (made of borosilicate glass) was replaced with nitrogen, and 84 g of reduced coenzyme Q10 and 340 g of 99.5% ethanol were then added thereto (reduced coenzyme Q10 concentration: 20 wt. %). Thereafter, the obtained raw material mixture was warmed to 50° C. while stirring with a stirring blade (power required for stirring: 0.3 kw/m$^3$) to obtain a homogeneous solution. This solution was cooled to 40° C., and thereafter, 0.8 g (1 wt. %) of reduced coenzyme Q10 crystals comprising reduced coenzyme Q10 Form II crystals were added as seed crystals to the solution, and the mixture thus obtained was kept at 40° C. for 3 hours to precipitate crystals. Thereafter, the mixture was cooled to 35° C. over 6 hours, was then retained at 35° C. for 24 hours, and was then filtered for solid-liquid separation. The obtained crystal was dried under reduced pressure at 47° C. for 4 hours to obtain a reduced coenzyme Q10 Form II crystal (Form II rate: 100%; recovery rate: 91%).

Example 2

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 38° C., and thereafter, 0.55 g (1 wt. %) of reduced coenzyme Q10 crystals comprising reduced coenzyme Q10 Form II crystals were added as seed crystals to the solution, and the mixture thus obtained was kept at 38° C. for 23 hours to precipitate crystals. Thereafter, the mixture was cooled to 25° C. over 1 hour, was then kept at 25° C. for 1 hour, and was then filtered for solid-liquid separation. The obtained crystal was dried under reduced pressure at 49° C. for 4 hours to obtain a reduced coenzyme Q10 Form II crystal (Form II rate: 100%; recovery rate: 98%). Besides, the crystals after the solid-liquid separation and before drying were sampled, and the rate of Form II was measured. As a result, the rate of Form II was 100%.

Example 3

The inside of a 100 mL three-necked flask (made of borosilicate glass) was replaced with nitrogen, and 50 g of reduced coenzyme Q10 and 33 g of n-hexane were then added thereto (reduced coenzyme Q10 concentration: 60 wt. %). Thereafter, the obtained raw material mixture was warmed to 50° C. while stirring with a stirring blade (power required for stirring: 0.3 kw/m$^3$) to obtain a homogeneous solution. This solution was cooled to 38° C., and thereafter, 0.5 g (1 wt. %) of reduced coenzyme Q10 crystals comprising reduced coenzyme Q10 Form II crystals were added as seed crystals to the solution, and the mixture thus obtained was kept at 38° C. for 5 hours to precipitate crystals. Thereafter, the mixture was cooled to 25° C. over 1 hour, was then kept at 25° C. for 14 hours, and was then filtered for solid-liquid separation. The obtained crystal was dried under reduced pressure at 40° C. to obtain a reduced coenzyme Q10 Form II crystal (Form II rate: 100%; recovery rate: 67%). Besides, the rate of Form II in the crystals after the solid-liquid separation and before drying was also 100%.

Example 4

The inside of a 100 mL three-necked flask (made of borosilicate glass) was replaced with nitrogen, and 10 g of reduced coenzyme Q10 and 48.8 g of acetonitrile were then added thereto (reduced coenzyme Q10 concentration: 17 wt. %). Thereafter, the obtained raw material mixture was warmed to 50° C. while stirring with a stirring blade (power required for stirring: 0.3 kw/m$^3$) to obtain a homogeneous solution. This solution was cooled to 38° C., and thereafter, 0.1 g (1 wt. %) of reduced coenzyme Q10 crystals comprising reduced coenzyme Q10 Form II crystals were added as seed crystals to the solution, and the mixture thus obtained was kept at 38° C. for 5 hours to precipitate crystals. Thereafter, the mixture was cooled to 25° C. over 1 hour, was then kept at 25° C. for 14 hours, and was then filtered for solid-liquid separation. The obtained crystal was dried under reduced pressure at 40° C. to obtain a reduced coenzyme Q10 Form II crystal (Form II rate: 22%; recovery rate: 99%). Besides, the rate of Form II in the crystals after the solid-liquid separation and before drying was also 22%.

Example 5

The inside of a 100 mL three-necked flask (made of borosilicate glass) was replaced with nitrogen, and 50 g of reduced coenzyme Q10 and 16.7 g of ethyl acetate containing 7% by weight of water were then added thereto (reduced coenzyme Q10 concentration: 75 wt. %). Thereafter, the obtained raw material mixture was warmed to 50° C. while stirring with a stirring blade (power required for stirring: 0.3 kw/m$^3$) to obtain a homogeneous solution. This solution was cooled to 38° C., and thereafter, 0.5 g (1 wt. %) of reduced coenzyme Q10 crystals comprising reduced coenzyme Q10 Form II crystals were added as seed crystals to the solution, and the mixture thus obtained was kept at 38° C. for 5 hours to precipitate crystals. Thereafter, the mixture was cooled to 25° C. over 1 hour, was then kept at 25° C. for 14 hours, and was then filtered for solid-liquid separation. The obtained crystal was dried under reduced pressure at 40° C. to obtain a reduced coenzyme Q10 Form II crystal (Form II rate: 100%; recovery rate: 60%). Besides, the rate of Form II in the crystals after the solid-liquid separation and before drying was also 100%.

Example 6

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 40° C., and thereafter, 0.55 g (1 wt. %) of reduced coenzyme Q10 crystals comprising reduced coenzyme Q10 Form II crystals were added as seed crystals to the solution, and the mixture thus obtained was kept at 40° C. for 23 hours to precipitate crystals. Thereafter, the mixture was cooled to 25° C. over 8 hours, was then kept at 25° C. for 1 hour, and was then filtered for solid-liquid separation. The obtained crystal was dried under reduced pressure at 46° C. for 15 hours to obtain a reduced coenzyme Q10 Form II crystal (Form II rate: 100%; recovery rate: 97%). Besides, the rate of Form II in the crystals after the solid-liquid separation and before drying was also 100%.

Example 7

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 42° C., and thereafter, 0.55 g (1 wt. %) of reduced coenzyme Q10 crystals comprising reduced coenzyme Q10 Form II crystals were added as seed crystals to the solution, and the mixture thus obtained was kept at 42° C. for 18 hours to precipitate crystals. Thereafter, the mixture was cooled to 25° C. over 2 hours, was then kept at 25° C. for 1 hour, and was then filtered for solid-liquid separation. The obtained crystal was dried under reduced pressure at 47° C. for 15 hours to obtain a reduced coenzyme Q10 Form II crystal (Form II rate: 40%; recovery rate: 99%).

Example 8

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 32° C., and thereafter, 0.55 g (1 wt. %) of reduced coenzyme Q10 crystals comprising reduced coenzyme Q10 Form II crystals were added as seed crystals to the solution, and the mixture thus obtained was kept at 32° C. for 23 hours, and was then filtered for solid-liquid separation. The obtained crystal was dried under reduced pressure at 40° C. to obtain a reduced coenzyme Q10 Form II crystal (Form II rate: 70%; recovery rate: 95%). Besides, the rate of Form II in the crystals after the solid-liquid separation and before drying was also 70%.

Comparative Example 1

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 45° C., and thereafter, 0.55 g (1 wt. %) of reduced coenzyme Q10 crystals comprising reduced coenzyme Q10 Form II crystals were added as seed crystals to the solution, and the mixture thus obtained was kept at 45° C. for 1 hour. Thereafter, the reaction mixture was confirmed by visual observation. As a result, no crystals were precipitated, and the seed crystals were all dissolved in the solution.

Comparative Example 2

The inside of a 500 mL separable flask (made of borosilicate glass) was replaced with nitrogen, and 55 g of reduced coenzyme Q10 and 368 g of 95% ethanol (water content: 7.6% by weight) were then added thereto (reduced coenzyme Q10 concentration: 13 wt. %). Thereafter, the obtained raw material mixture was warmed to 50° C. while stirring with a stirring blade (power required for stirring: 0.3 kw/m$^3$) to obtain a homogeneous solution. This solution was cooled to 30° C., and thereafter, 0.55 g (1 wt. %) of reduced coenzyme Q10 crystals comprising reduced coenzyme Q10 Form II crystals were added as seed crystals to the solution, and the mixture thus obtained was kept at 30° C. for 24 hours, and was then filtered for solid-liquid separation. The obtained crystal was dried under reduced pressure at 40° C. to obtain a reduced coenzyme Q10 crystal (recovery rate: 95%). The rate of Form II in the obtained reduced coenzyme Q10 crystal was 0%.

Example 9

The inside of a 500 mL separable flask (made of borosilicate glass) was replaced with nitrogen, and 46.5 g of reduced coenzyme Q10 and 376.5 g of 85% ethanol (water content: 15 by weight) were then added thereto (reduced coenzyme Q10 concentration: 11 wt. %). Thereafter, the obtained raw material mixture was warmed to 50° C. while stirring with a stirring blade (power required for stirring: 0.3 kw/m$^3$) to obtain a homogeneous solution. This solution was cooled to 40° C., and thereafter, 0.465 g (1 wt. %) of reduced coenzyme Q10 crystals comprising reduced coenzyme Q10 Form II crystals were added as seed crystals to the solution, and the mixture thus obtained was kept at 40° C. for 17 hours, and was then filtered for solid-liquid separation. The obtained crystal was dried under reduced pressure at 40° C. to obtain a reduced coenzyme Q10 Form II crystal (Form II rate: 80%; recovery rate: 98%). Besides, the rate of Form II in the crystals after the solid-liquid separation and before drying was also 80%.

Example 10

The inside of a 500 mL separable flask (made of borosilicate glass) was replaced with nitrogen, and 55 g of reduced coenzyme Q10 and 403 g of 99.5% ethanol were then added thereto (reduced coenzyme Q10 concentration: 12 wt. %). Thereafter, the obtained raw material mixture was warmed to 50° C. while stirring with a stirring blade (power required for stirring: 0.03 kw/m$^3$) to obtain a homogeneous solution. This solution was cooled to 36° C., and thereafter, 2.5 g (5 wt. %) of reduced coenzyme Q10 crystals comprising reduced coenzyme Q10 Form II crystals were added as seed crystals to the solution, and the mixture thus obtained was kept at 36° C. for 24 hours to precipitate crystals. Thereafter, the mixture was cooled to 10° C. over 26 hours, was then kept at 10° C. for 1 hour, and was then filtered for solid-liquid separation. The obtained crystal was dried under reduced pressure at 45° C. to obtain a reduced coenzyme Q10 Form II crystal (Form II rate: 100%; recovery rate: 97%).

Comparative Example 3

The inside of a 500 mL separable flask (made of borosilicate glass) was replaced with nitrogen, and 144 g of reduced coenzyme Q10 and 479 g of acetone were then added thereto (reduced coenzyme Q10 concentration: 23 wt. %). Thereafter, the obtained raw material mixture was warmed to 50° C. while stirring with a stirring blade (power required for stirring: 0.3 kw/m$^3$) to obtain a homogeneous solution. This solution was cooled to 38° C., and thereafter, 1.44 g (1 wt. %) of reduced coenzyme Q10 crystals comprising reduced coenzyme Q10 Form II crystals were added as seed crystals to the solution, and the mixture thus obtained was kept at 38° C. for 5 hours to precipitate crystals. Thereafter, the mixture was cooled to 25° C. over 1 hour, was then kept at 25° C. for 1 hour, and was then filtered for solid-liquid separation. The obtained crystal was dried under reduced pressure at 45° C. to obtain a reduced coenzyme Q10 crystal (recovery rate: 78%). The rate of Form II in the obtained reduced coenzyme Q10 crystal was 0%.

Example 11

The inside of a 500 mL separable flask (made of borosilicate glass) was replaced with nitrogen, and 40.0 g of reduced coenzyme Q10 and 360 g of 99.5% ethanol were then added thereto (reduced coenzyme Q10 concentration: 10 wt. %). Thereafter, the obtained raw material mixture was warmed to 42° C. while stirring with a stirring blade (power required for stirring: 0.1 kw/m$^3$) to obtain a homogeneous solution. This solution was cooled to 35° C., and thereafter, 0.4 g (1 wt. %) of reduced coenzyme Q10 crystals comprising reduced coenzyme Q10 Form II crystals were added as seed crystals to the solution.

The mixture obtained after the addition of the seed crystals was kept at 35° C. for 15 hours to precipitate crystals. Thereafter, the mixture was cooled to 25° C. at a constant cooling rate of −2° C./hour over 5 hours, and was then cooled to 10° C. at a constant cooling rate of −10° C./hour over 1.5 hours, to further precipitate crystals. After the temperature had reached 10° C., the mixture was filtered for solid-liquid separation. The obtained crystal was dried under reduced pressure at 35° C. for 10 hours to obtain a reduced coenzyme Q10 Form II crystal (Form II rate: 100%; recovery rate: 97%).

In the present experiment, the liquid phase of the mixture was sampled immediately before addition of the seed crystals (at 0 hour), and then at 3 hours, 6 hours, 9 hours, 12 hours, 15 hours (so far, at 35° C.), 17.5 hours (30° C.), 20 hours (25° C.), 20.5 hours (20° C.), and 21.5 hours (10° C.) after the addition of the seed crystals. The concentration (wt. %) of reduced coenzyme Q10 dissolved in the liquid phase sample was measured according to high performance liquid chromatography. The measurement results are shown in the following table.

TABLE 1

| Crystallization time (h) | Temperature (° C.) | Reduced coenzyme Q10 concentration (wt %) |
| --- | --- | --- |
| 0 | 35 | 10.0 |
| 3 | 35 | 9.9 |
| 6 | 35 | 9.6 |
| 9 | 35 | 9.2 |
| 12 | 35 | 8.5 |
| 15 | 35 | 7.2 |
| 17.5 | 30 | 3.1 |
| 20 | 25 | 1.5 |
| 20.5 | 20 | 0.8 |
| 21.5 | 10 | 0.3 |

Conditions for the high performance liquid chromatography, by which the reduced coenzyme Q10 concentration was measured, are shown below.

(HPLC Conditions)
Column: SYMMETRY C18 (manufactured by Waters); 250 mm (length), 4.6 mm (inner diameter)
Mobile phase: $C_2H_5OH:CH_3OH=4:3$ (v:v)
Detection wavelength: 210 nm
Flow rate: 1 ml/min
Retention time of reduced coenzyme Q10: 9.1 min.

All publications, patents and patent applications cited in the present description are incorporated herein by reference in their entirety.

The invention claimed is:

1. A method for producing a reduced coenzyme Q10 Form II crystal, comprising:
    adding a reduced coenzyme Q10 Form II crystal as a seed crystal to a solution with a temperature of 32° C. to 43° C., said solution comprising (a) at least one organic solvent selected from the group consisting of an alcohol, a hydrocarbon, an aliphatic acid ester and a nitrogen compound, and (b) reduced coenzyme Q10, to prepare a mixture, and
    precipitating the reduced coenzyme Q10 from the mixture, in the form of the reduced coenzyme Q10 Form II crystal;
    wherein the reduced coenzyme Q10 Form II crystal is obtained with a Form II rate of 70-100%; or
    wherein the reduced coenzyme Q10 Form II crystal is obtained with a recovery rate of 78-99%.

2. The method according to claim 1, wherein an amount of the seed crystal added is 0.5% to 20% by weight, based on a weight of the reduced coenzyme Q10 in the solution before the addition of the seed crystal.

3. The method according to claim 1, wherein the organic solvent comprises 0.5% to 34% by weight of water.

4. The method according to claim 1, wherein the organic solvent is a monohydric alcohol having 1 to 5 carbon atoms.

5. The method according to claim 4, wherein the monohydric alcohol having 1 to 5 carbon atoms is ethanol.

6. The method according to claim 5, wherein the ethanol comprises 8% by weight or less of water or does not comprise water.

7. The method according to claim 1, further comprising, before the preparation of the mixture,
    heating a raw material mixture containing the organic solvent and the reduced coenzyme Q10 to 42° C. or higher, so that the reduced coenzyme Q10 is dissolved in the organic solvent, and
    cooling the solution resulting after the heating to a temperature that is lower than the heating temperature and in the range of 32° C. to 43° C., to prepare a solution of the reduced coenzyme Q10, wherein the solution is supersaturated.

8. The method according to claim 1, wherein the precipitating the reduced coenzyme Q10 comprises maintaining the temperature of the mixture at 32° C. or higher for 1 hour or more after the adding the seed crystal.

9. The method according to claim 1, wherein the precipitating the reduced coenzyme Q10 comprises decreasing over time the temperature of the mixture.

10. The method according to claim 1, wherein the precipitating the crystal comprises:
    maintaining the temperature of the mixture at 32° C. or higher for 1 hour or more after the adding the seed crystal, and then,
    decreasing the temperature of the mixture to a temperature of 25° C. or lower at a rate in which a temperature decrease amount per hour is 15° C. or lower.

11. The method according to claim 1, wherein the precipitating the crystal is carried out, while forced-flowing the mixture with a power required for stirring of 0.03 kw/m$^3$ or more per unit volume.

12. The method according to claim 1, wherein the solution contains 1% by weight or more and 70% by weight or less of reduced coenzyme Q10.

13. The method according to claim 1, further comprising solid-liquid separating the precipitated crystal and then drying the precipitated crystal at a temperature of 46° C. or higher.

14. The method according to claim 1, which is carried out under a deoxygenated atmosphere.

15. The method according to claim 1, which is carried out under industrial scale production.

* * * * *